US010550050B2

(12) United States Patent
Paek et al.

(10) Patent No.: US 10,550,050 B2
(45) Date of Patent: *Feb. 4, 2020

(54) PROCESSES FOR SEPARATING DIMETHYL BIPHENYL ISOMERS USING ZEOLITE ADSORBENTS

(71) Applicant: ExxonMobil Research and Engineering Company, Annandale, NJ (US)

(72) Inventors: Changyub Paek, Bridgewater, NJ (US); Michael P. Lanci, Flemington, NJ (US); Randall D. Partridge, Califon, NJ (US); Allen W. Burton, Stewartsville, NJ (US); Carla S. Pereira, Bridgewater, NJ (US); Benjamin A. McCool, Annandale, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 12 days.

This patent is subject to a terminal disclaimer.

(21) Appl. No.: 15/886,199

(22) Filed: Feb. 1, 2018

(65) Prior Publication Data

US 2018/0215685 A1 Aug. 2, 2018

Related U.S. Application Data

(60) Provisional application No. 62/453,190, filed on Feb. 1, 2017.

(51) Int. Cl.
*C07C 2/74* (2006.01)
*C07C 15/14* (2006.01)
(Continued)

(52) U.S. Cl.
CPC .............. *C07C 2/74* (2013.01); *B01D 15/08* (2013.01); *B01J 20/186* (2013.01);
(Continued)

(58) Field of Classification Search
None
See application file for complete search history.

(56) References Cited

U.S. PATENT DOCUMENTS 3,626,020 A 12/1971 Neuzil
3,699,182 A 10/1972 Cattanach
(Continued)

FOREIGN PATENT DOCUMENTS

WO 2014117076 A1 7/2014
WO 2014117076 A9 7/2015
(Continued)

OTHER PUBLICATIONS

Baertsch et al., "Permeation of aromatic hydrocarbon vapors through silicalite-zeolite membranes", J. Phys. Chem, 1996, vol. 100, pp. 7676-7679.
(Continued)

*Primary Examiner* — Tam M Nguyen
(74) *Attorney, Agent, or Firm* — Priya G. Prasad; Kristina M. Okafor

(57) ABSTRACT

In a process for separating one or more 3,3'-, 3,4'- and 4,4'-dimethyl biphenyl isomers, a feed comprising the isomers is contacted with a zeolite adsorbent which contains one or more metal cations in the +1 or +2 oxidation states. Separation processes for each of the 3,3'-, 3,4'- and 4,4'-dimethyl biphenyl isomers is provided.

34 Claims, 8 Drawing Sheets

(51) Int. Cl.

| | | |
|---|---|---|
| *C07C 7/13* | (2006.01) | |
| *B01J 20/28* | (2006.01) | |
| *B01J 20/18* | (2006.01) | |
| *B01D 15/08* | (2006.01) | |
| *C07C 2/66* | (2006.01) | |
| *C07C 5/10* | (2006.01) | |
| *C07C 5/27* | (2006.01) | |
| *C07C 5/367* | (2006.01) | |

(52) U.S. Cl.
CPC ........... *B01J 20/28007* (2013.01); *C07C 2/66* (2013.01); *C07C 5/10* (2013.01); *C07C 5/2732* (2013.01); *C07C 5/367* (2013.01); *C07C 7/13* (2013.01); *C07C 15/14* (2013.01)

(56) References Cited

U.S. PATENT DOCUMENTS

| | | | |
|---|---|---|---|
| 6,730,625 | B1 | 5/2004 | Chang et al. |
| 8,580,120 | B2 | 11/2013 | Porter |
| 9,085,669 | B2 | 7/2015 | Dakka et al. |
| 9,328,053 | B2 | 5/2016 | Bai et al. |
| 9,580,572 | B2 | 2/2017 | Dakka et al. |
| 9,663,417 | B2 | 5/2017 | Dakka et al. |
| 9,688,602 | B2 | 6/2017 | Dakka et al. |
| 9,896,393 | B2 | 2/2018 | Salciccioli et al. |
| 2009/0326310 | A1 | 12/2009 | Kulprathipanja et al. |
| 2016/0176785 | A1 | 6/2016 | Salciccioli et al. |

FOREIGN PATENT DOCUMENTS

| | | |
|---|---|---|
| WO | 2015112252 A1 | 7/2015 |
| WO | 20150191289 A1 | 12/2015 |

OTHER PUBLICATIONS

Foster et al., "A geometric solution to the largest-free-sphere problem in zeolite frameworks", Micropo. Mesopor. Mat., 2006, vol. 90, pp. 32-38.

Funke et al., "Separation of close-boiling hydrocarbons with silicalite zeolite", J. Chem. Soc. Faraday Trans., 1996, vol. 92, pp. 2499-2502.

Minceva et al., "Modeling and simulation of a simulated moving bed for the separation of p-xylene", Ind. Eng. Chem. Res., 2002, vol. 41, pp. 3454-3461.

Minceva et al., "Understanding and revamping of industrial scale SMB units for p-xylene separation", AIChE Journal, 2007, vol. 53, pp. 138-149.

Pais et al., "Chiral separation by SMB chromatography", Sep. Pur. Tech., 2000, vol. 20, pp. 67-77.

Rajendran et al., "Simulated moving bed chromatography for the separation of enantiomers", J. Chrom. A, 2009, vol. 1216, pp. 709-738.

Silva et al., "Fixed-bed adsorption of aromatic C8 isomers: Breakthrough experiments, modeling and simulation", 2012, vol. 90, pp. 246-256.

Silva et al., "Modeling and simulation of an industrial-scale parex process", AIChE Journal, 2015, vol. 61, pp. 1345-1363.

Tokay et al., "Nanopaiticle silicalite-1 crystallization from clear solutions: Nucleation", Micropor. Mesopor. Mat., 2009, vol. 118, pp. 143-151.

Ruthven et al., "Counter-Current and Simulated Counter-Current Adsorption Separation Processes", Chem. Eng. Sci., 1989, vol. 44, pp. 1011-1038.

PROCESSES FOR SEPARATING DIMETHYL BIPHENYL ISOMERS USING ZEOLITE ADSORBENTS

CROSS-REFERENCE TO RELATED APPLICATIONS

This application claims the benefit of U.S. Provisional Application No. 62/453,190, filed on Feb. 1, 2017, the entire contents of which are incorporated herein by reference.

FIELD

The present disclosure relates to processes for separating one or more of 3,3'-, 3,4'- and 4,4'-dimethyl biphenyl (DMBP) isomers from mixtures comprising the isomers. The disclosure also relates to processes for modifying the relative amounts of the DMBP isomers in such mixtures. The processes are facilitated by zeolite adsorbents, particularly zeolites modified by metal cations.

BACKGROUND

Dimethyl biphenyl (DMBP) compounds are useful intermediates in the production of a variety of commercially valuable products, including polyesters and plasticizers for PVC and other polymer compositions. DMBP compounds can be readily converted to an ester plasticizer by a process comprising oxidation of the DMBP to produce the corresponding mono- or dicarboxylic acid followed by esterification with a long chain alcohol.

For example, 4,4'-biphenyl-dicarboxylic acid, optionally together with 3,4'-biphenyl dicarboxylic acid, is a potential precursor, either alone or as a modifier for polyethylene terephthalate (PET), in the production of polyester fibers, engineering plastics, liquid crystal polymers for electronic and mechanical devices, and films with high heat resistance and strength.

Processes to produce DMBP compounds generally yield a mixture of all six DMBP isomers, namely 2,2'-, 2,3'-, 2,4'-, 3,3'-, 3,4'- and 4,4'-DMBP (see, for example, International Patent Application Publication No. WO 2015/112252).

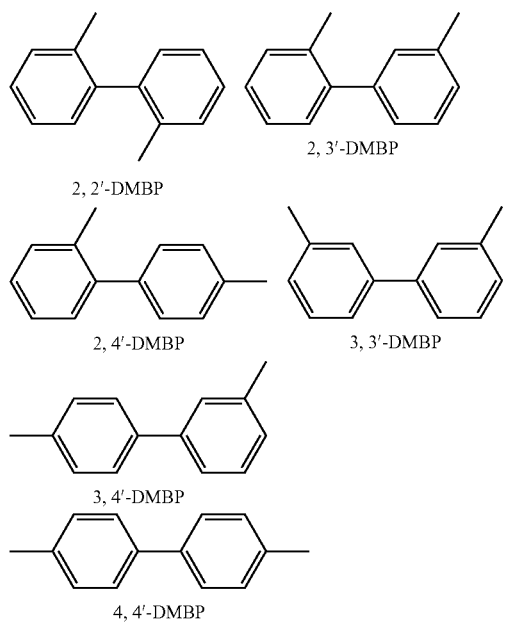

However, for certain applications, it is desirable to maximize the purity of individual isomers, particularly the 3,3'-, 3,4'- and 4,4'-isomers.

Based on boiling point differences it is possible to separate the 3,3'-, 3,4'- and 4,4'-isomers from the 2,X' isomers, where X=2, 3 or 4, utilizing, for example, fractional distillation. However, separation of the 3,3'-, 3,4'- and 4,4'-isomers from each other based on boiling point is more challenging, particularly separation of the 3,4'-isomer from the 4,4'-isomer which have very close boiling points (see Table 1 below).

TABLE 1

| Isomer | Normal Boiling Point (° C.) | Fusion Temperature (° C.) |
| --- | --- | --- |
| 2,2' | 261 | 19 |
| 2,3' | 272 | |
| 2,4' | 275 | −24 |
| 3,3' | 289 | 8 |
| 3,4' | 293 | 11 |
| 4,4' | 296 | 115 |

Further, based on heat of fusion differences it is in principle possible to effect separation of 3,3'-, 3,4'- and 4,4'-isomers via crystallization. However, because the relative proportions of some of these isomers in a given mixture may be small, separation via crystallization may not be commercially attractive.

It is known that certain adsorbents, for example zeolites, can be used to separate individual hydrocarbons from mixtures thereof. Adsorptive separation may be useful where the components to be separated have similar physical properties such as boiling point and melting point. For example, utilizing zeolites it is possible to selectively separate a predetermined xylene from a mixture of xylene isomers. See, for example, United States Patent Application Publication No. 2009/0326310 and references therein.

In view of the above it would be desirable to provide alternative processes for the separation of 3,3'-, 3,4'- and 4,4'-DMBP isomers, particularly processes that may be amenable to commercial implementation.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

SUMMARY

In a first aspect of the present disclosure there is provided a process for separating one or more of the dimethyl biphenyl (DMBP) isomers, 3,3'-DMBP, 3,4'-DMBP and/or 4,4'-DMBP from a mixture comprising two or more of said isomers, the process comprising a step of contacting said mixture with an adsorbent comprising at least one zeolite, wherein said zeolite comprises one or more metal cations in the +1 or +2 oxidation states.

In a second aspect of the present disclosure there is provided a process for modifying the relative amounts of the dimethyl biphenyl (DMBP) isomers, 3,3'-DMBP, 3,4'-DMBP and/or 4,4'-DMBP in a mixture comprising two or more of said isomers, the process comprising a step of contacting said mixture with an adsorbent comprising at least one zeolite, wherein said zeolite comprises one or more metal cations in the +1 or +2 oxidation states.

In both the foregoing aspects said zeolite may have a largest diffuse along dimension of at least about 4 Angstroms (Å).

As used herein the term 'zeolite', as well as encompassing aluminosilicate materials, also encompasses zeolite analogues where one or more of the framework aluminum and/or silicon atoms are replaced by another atom, such as, for example, boron, gallium, germanium, magnesium, titanium, phosphorus, nitrogen or sulfur.

As used herein the term 'largest diffuse along dimension' refers to a measure of the largest dimension of a zeolite channel system based on the diameter of the largest possible free-sphere that can diffuse along dimensions a, b or c of a zeolite channel and which are computed geometrically by Delaunay triangulation as detailed in: "A geometric solution to the largest-free-sphere problem in zeolite frameworks", M. D. Foster, I. Rivin, M. M. J. Treacy and O. Delgado Friedrichs, *Micropor. Mesopor. Mat.*, 90, 32-38, 2006.

In both the foregoing aspects of the present disclosure the largest diffuse along dimension of the zeolite may be at least about 4.5 Å, or at least about 5.0 Å, or at least about 5.5 Å, or at least about 6.0 Å, or at least about 6.5 Å, or at least about 7.0 Å.

In both the foregoing aspects of the present disclosure the largest diffuse along dimension of the zeolite may be between about 4.0 Å and about 8.0 Å, or between about 4.5 Å and about 8.0 Å, or between about 5.0 Å and about 8.0 Å, or between about 5.5 Å and about 8.0 Å, or between about 6.0 Å and about 8.0 Å, or between about 6.5 Å and about 8.0 Å.

In both the foregoing aspects of the present disclosure the zeolite structure type may comprise BEA, FAU, MFI, MEL, MTW, MOR, LTL, EMT, FER, MAZ, MEI, TON, MWW, EUO, MFS, IMF, MRE, ITN, MTT, MSE or IWV.

In both the foregoing aspects of the present disclosure the zeolite may comprise a 12-ring zeolite, an 11-ring zeolite or a 10-ring zeolite.

In both the foregoing aspects the zeolite may comprise an X or Y type zeolite or a Beta type zeolite.

The Si/Al ratio of the zeolite may be less than about 200, or less than about 100, or less than about 50, or less than about 20, or less than about 10. The Si/Al ratio may preferably be less than about 10.

In some embodiments the Si/Al ratio of the zeolite may be between about 1 and about 4, or between about 1.5 and about 3.5, or between about 2 and about 3.

The zeolite may comprise one or more alkali metal cations, alkaline earth metal cations, transition metal cations, rare earth metal cations or combinations thereof.

The zeolite may comprise one or more alkali metal cations, alkaline earth metal cations or combinations thereof.

the zeolite may comprise one or more of Na+, K+, Rb+, Cs+, Mg2+, Ca2+, Sr2+ and Ba2+ cations.

The zeolite may comprise one or more metal cations, wherein the ionic radius of the metal cation is between about 0.8 Å and about 2.0 Å.

In some embodiments the molar ratio of all metal cations in the +1 and/or +2 oxidation states relative to aluminum in the zeolite may be between about 0.01 and about 2.0, or between about 0.05 and about 1.5, or between about 0.1 and about 1.5, or between about 0.25 and about 1.5.

In some embodiments the molar ratio of all metal cations in the +1 and/or +2 oxidation states relative to aluminum in the zeolite may be greater than about 0.27, or greater than about 0.30, or greater than about 0.40, or greater than about 0.45, or greater than about 0.50.

In some embodiments the zeolites used to prepare the adsorbents of the present disclosure contain residual amounts of sodium cations. This is because the originally prepared zeolite may have used sodium containing compounds in its synthesis, for example in the case of a Y type zeolite. The amount of residual sodium cations may depend on the level of other metal cation exchange that has occurred during the cation exchange process.

In some embodiments the Na/Al molar ratio of the zeolite is less than about 1.0, or less than about 0.8, or less than about 0.6, or less than about 0.4, or less than about 0.3 when the zeolite contains at least one other metal cation.

In some embodiments the molar ratio of metal cations in the +1 and/or +2 oxidation states other than sodium, and relative to aluminum in the zeolite, may be greater than about 0.1, or greater than about 0.2, or greater than about 0.3, or greater than about 0.4. Preferably, the ratio is greater than about 0.3.

Metal cations modify the relative adsorption of the dimethyl biphenyl isomers to a degree that the order of preference for adsorption is changed.

In some embodiments the average crystallite size of the zeolite may be less than about 5000 nm, or less than about 2000 nm, or less than about 1000 nm, or less than about 500 nm, or less than about 200 nm, or less than about 100 nm, or less than about 50 nm.

In some embodiments the average crystallite size of the zeolite may be from about 1 to about 5000 nm, or from about 1 to about 2000 nm, or from about 1 to about 1000 nm, or from about 5 to about 500 nm, or from about 10 to about 50 nm.

In some embodiments the processes disclosed herein comprise separating 3,3'-DMBP from a mixture comprising two or more of 3,3'-DMBP, 3,4'-DMBP and 4,4'-DMBP.

In some embodiments the processes disclosed herein comprise separating 3,4'-DMBP from a mixture comprising two or more of 3,3'-DMBP, 3,4'-DMBP and 4,4'-DMBP.

In some embodiments the processes disclosed herein comprise separating 4,4'-DMBP from a mixture comprising two or more of 3,3'-DMBP, 3,4'-DMBP and 4,4'-DMBP.

In some embodiments the processes disclosed herein comprise modifying the relative amounts of 3,3'-DMBP, 3,4'-DMBP and/or 4,4'-DMBP in a mixture comprising two or more of 3,3'-DMBP, 3,4'-DMBP and 4,4'-DMBP.

In some embodiments the processes disclosed herein comprise reducing the relative amount of 3,3'-DMBP in a mixture comprising two or more of 3,3'-DMBP, 3,4'-DMBP and 4,4'-DMBP.

In some embodiments the processes disclosed herein comprise reducing the relative amount of 3,4'-DMBP in a mixture comprising two or more of 3,3'-DMBP, 3,4'-DMBP and 4,4'-DMBP.

In some embodiments the processes disclosed herein comprise reducing the relative amount of 4,4'-DMBP in a mixture comprising two or more of 3,3'-DMBP, 3,4'-DMBP and 4,4'-DMBP.

In one embodiment the process comprises separating 3,3'-DMBP from a mixture comprising two or more of 3,3'-DMBP, 3,4'-DMBP and 4,4'-DMBP, wherein the zeolite comprises one or more metal cations in the +1 or +2 oxidation states and wherein the zeolite has a largest diffuse along dimension of at least about 4 Angstroms (Å).

In one embodiment the process comprises separating 3,4'-DMBP from a mixture comprising two or more of 3,3'-DMBP, 3,4'-DMBP and 4,4'-DMBP, wherein the zeolite comprises one or more metal cations in the +1 or +2 oxidation states and wherein the zeolite has a largest diffuse along dimension of at least about 4 Angstroms (Å).

In one embodiment the process comprises separating 4,4'-DMBP from a mixture comprising two or more of 3,3'-DMBP, 3,4'-DMBP and 4,4'-DMBP, wherein the zeolite comprises one or more metal cations in the +1 or +2 oxidation states and wherein the zeolite has a largest diffuse along dimension of at least about 4 Angstroms (Å).

In other embodiments two different adsorbents which have different adsorption characteristics for the three DMBP isomers may be utilized. For example, two different adsorbents in series operation.

A first selective adsorption may preferentially adsorb one of the 3,3'-, 3,4'- or 4,4'-dimethyl biphenyl isomers and a second selective adsorption may preferentially adsorb one of the 3,3'-, 3,4'- or 4,4'-dimethyl biphenyl isomers not preferentially adsorbed in the first selective adsorption.

A first selective adsorption may preferentially adsorb two of the 3,3'-, 3,4'- or 4,4'-dimethyl biphenyl isomers and after desorption of the two isomers, a second selective adsorption may preferentially adsorb one of them.

Accordingly, the use of two different adsorbents may provide a process for separating a mixture of the three DMBP isomers into pure components.

The mixture of DMBP isomers may further comprise one or more solvents. A wide range of solvents are contemplated. Preferred solvents include saturated hydrocarbons and aromatic hydrocarbons and mixtures thereof.

It has further been surprisingly discovered that particular solvent/metal cation combinations improve the separation of particular DMBP isomers.

In some embodiments of the processes of the present disclosure the degree of separation of the 3,3'-DMBP, 3,4'-DMBP and 4,4'-DMBP isomers may be based on the kinetic diameter of the solvent. The kinetic diameter may be derived from a spherical model or a smallest ellipsoid model. In other embodiments the degree of separation may be based on the polarity of the solvent. In yet other embodiments the degree of separation may be based on both the kinetic diameter of the solvent and its polarity. Accordingly, solvents which are bulkier (generally a larger kinetic diameter) may afford improved separation of the isomers, however this effect may be modulated by solvent polarity. Generally, single ring aromatic solvents such as benzene adsorb to the zeolite more strongly that saturated solvents.

Without wishing to be bound by theory it is believed that there is a tertiary interaction involving the DMBP isomers, the solvent and the metal cation treated zeolite which impact on the efficacy of selective adsorption of one or more of the DMBP isomers. Preferred solvents may be those which do not significantly compete with a particular DMBP isomer in respect of adsorption into the pores of the zeolite. Accordingly, due to their higher polarity, aromatic solvents are more likely to be bulkier relative to aliphatic solvents in order to achieve comparable adsorption of DMBP.

The kinetic diameters of various solvents of relevance to the present disclosure are shown in Table 2 below (see J. Chem. Soc., Faraday Trans., 1996, 92, 2499-2502 and J. Phys. Chem, 1996, 100, 7676-7679).

TABLE 2

| Solvent | Kinetic Diameter (Å) |
| --- | --- |
| iso-octane | 6.2 |
| tri-isopropyl benzene | 8.5 |
| toluene | 5.9 |

TABLE 2-continued

| Solvent | Kinetic Diameter (Å) |
| --- | --- |
| p-xylene | 5.9 |
| m-xylene | 6.8 |
| mesitylene | 7.5 |

In some embodiments the solvent comprises a saturated organic solvent wherein the kinetic diameter of the solvent is greater than about 4.5 Å, or greater than about 5.0 Å, or greater than about 5.5 Å, or greater than about 6.0 Å.

In some embodiments the solvent comprises an aromatic organic solvent wherein the kinetic diameter of the solvent is greater than about 6.0 Å, or greater than about 6.5 Å, or greater than about 7.0 Å, or greater than about 7.5 Å.

In one embodiment the process comprises separating 3,3'-DMBP from a mixture comprising two or more of 3,3'-DMBP, 3,4'-DMBP and 4,4'-DMBP wherein the zeolite comprises one or more alkali metal cations, one or more alkaline earth cations or combinations thereof.

In another embodiment the process comprises separating 3,3'-DMBP from a mixture comprising two or more of 3,3'-DMBP, 3,4'-DMBP and 4,4'-DMBP wherein the zeolite comprises barium cations.

In another embodiment the process comprises separating 3,3'-DMBP from a mixture comprising two or more of 3,3'-DMBP, 3,4'-DMBP and 4,4'-DMBP wherein the zeolite comprises barium cations and wherein the solvent comprises iso-octane.

In one embodiment the process comprises separating 3,4'-DMBP from a mixture comprising two or more of 3,3'-DMBP, 3,4'-DMBP and 4,4'-DMBP wherein the zeolite comprises one or more alkali metal cations, one or more alkaline earth cations or combinations thereof.

In another embodiment the process comprises separating 3,4'-DMBP from a mixture comprising two or more of 3,3'-DMBP, 3,4'-DMBP and 4,4'-DMBP wherein the zeolite comprises potassium cations.

In another embodiment the process comprises separating 3,4'-DMBP from a mixture comprising two or more of 3,3'-DMBP, 3,4'-DMBP and 4,4'-DMBP wherein the zeolite comprises potassium cations and wherein the solvent comprises 1,3,5-trimethylbenzene.

In one embodiment the process comprises separating 4,4'-DMBP from a mixture comprising two or more of 3,3'-DMBP, 3,4'-DMBP and 4,4'-DMBP wherein the zeolite comprises one or more alkali metal cations, one or more alkaline earth cations or combinations thereof.

In another embodiment the process comprises separating 4,4'-DMBP from a mixture comprising two or more of 3,3'-DMBP, 3,4'-DMBP and 4,4'-DMBP wherein the zeolite comprises cesium cations.

In another embodiment the process comprises separating 4,4'-DMBP from a mixture comprising two or more of 3,3'-DMBP, 3,4'-DMBP and 4,4'-DMBP wherein the zeolite comprises cesium cations and wherein the solvent comprises iso-octane.

The person of ordinary skill in the art will appreciate that through selection of metal cation/solvent combinations, separation of all three of 3,3'-DMBP, 3,4'-DMBP and 4,4'-DMBP may be achieved.

In other embodiments two different adsorbents which have different adsorption characteristics for the three DMBP isomers may be utilized. For example, two adsorbents in series operation. These separations may be performed in the presence of the same or different solvents.

For example, a first selective adsorption may preferentially adsorb one of the 3,3'-, 3,4'- or 4,4'-dimethyl biphenyl isomers in the presence of a first solvent and after desorption of the isomers a second selective adsorption may preferentially adsorb one of them and in the presence of a second solvent which may be the same or different to the first solvent.

The first selective adsorption may preferentially adsorb two of the 3,3'-, 3,4'- or 4,4'-dimethyl biphenyl isomers in the presence of a first solvent and a second selective adsorption may preferentially adsorb one of the 3,3'-, 3,4'- or 4,4'-dimethyl biphenyl isomers preferentially adsorbed in the first selective adsorption and in the presence of a second solvent which may be the same or different to the first solvent.

Accordingly, the use of two different adsorbents either in the presence of the same or different solvents provides a process for separating a mixture of the three DMBP isomers into pure components.

The processes of the present disclosure may afford pure, substantially pure or enriched individual DMBP isomers. Purities of 3,3'-DMBP, 3,4'-DMBP and 4,4'-DMBP may, independently, be greater that 90 wt. %, or greater than 95 wt. %, or greater than 96 wt. %, or greater than 97 wt. % or greater than 98 wt. %, or greater than 99 wt. % or greater than 99.5 wt. % or greater than 99.9 wt. %.

The processes may be performed over a wide range of temperatures. Preferably the temperature is above about 20° C. or above about 115° C. The temperature may be between about 20° C. and about 300° C., or between about 20° C. and about 250° C., or between about 20° C. and about 200° C.

The processes may be performed in batch or continuous mode.

The contact time between the zeolite and the DMBP mixture may be between a few seconds and several hours, or between a few minutes and several hours, or between about 0.5 hours and about 10 hours, or between about 0.5 hours and about 5 hours.

In some embodiments the solvent heat of adsorption is less than a DMBP isomer heat of adsorption.

In some embodiments mixtures of solvents may be utilized to facilitate separation of the DMBP isomers. In other embodiments solvent gradients may be utilized to improve separation.

In some embodiments, the solvent or solvents used in the adsorptive separations may have a boiling point that is substantially lower than those of the DMBP isomers so as to facilitate separation of the solvents from the DMPB isomers by, for example, fractional distillation. In other embodiments a solvent of higher boiling point than those of the DMBP isomers may be utilized. In some embodiments both higher and lower boiling solvents may be used. In some embodiments the difference between the boiling point of the solvent or solvents and the boiling point of any one of the 3,3'-DMBP, 3,4'-DMBP and 4,4'-DMBP isomers is greater than about 100° C., or greater than about 75° C., or greater than about 50° C., or greater than about 25° C.

DETAILED DESCRIPTION OF THE EMBODIMENTS

Figure 1:
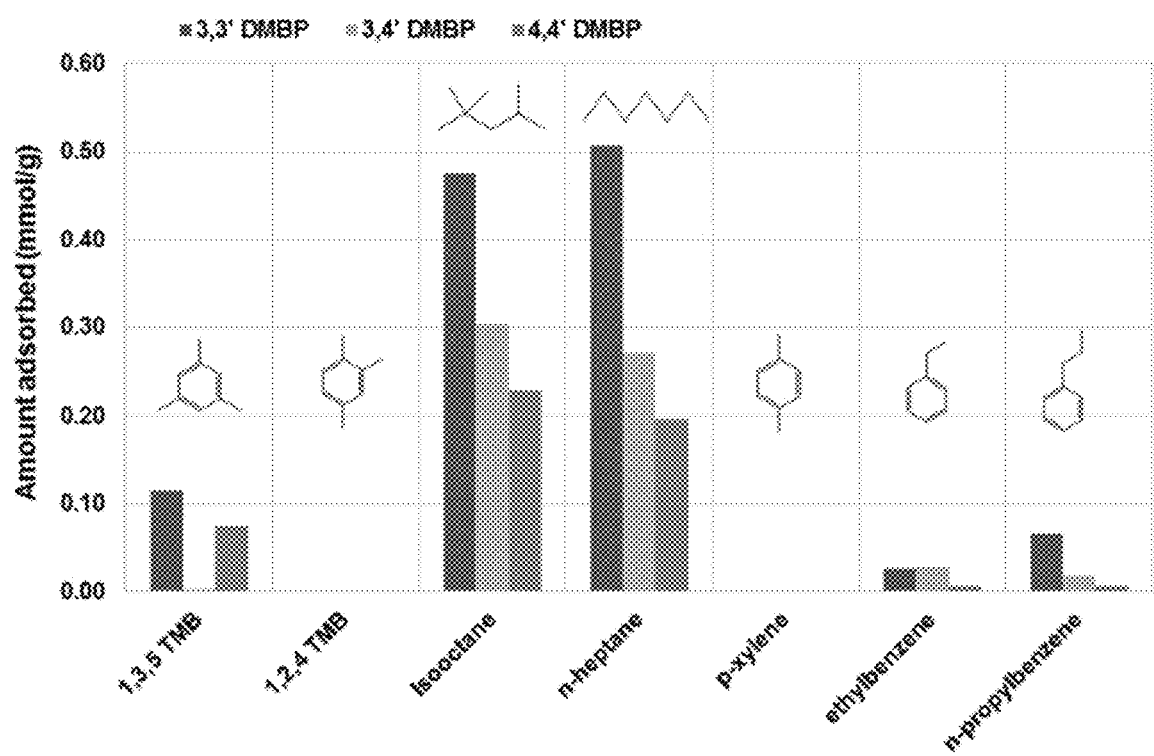
FIG. 1 is bar chart illustrating the effect of different solvents on the adsorption of 3,3'-DMBP, 3,4'-DMBP and 4,4'-DMBP on zeolite Y comprising potassium cations.

Before the present processes are disclosed and described, it is to be understood that unless otherwise indicated this disclosure is not limited to specific compositions, components, processes, or the like, as such may vary, unless otherwise specified. It is also to be understood that the terminology used herein is for the purpose of describing particular embodiments only and is not intended to be limiting.

It must also be noted that, as used in the specification and the appended claims, the singular forms 'a', 'an' and 'the' include plural referents unless otherwise specified. Thus, for example, reference to 'an alkaline earth metal cation' may include more than one alkaline earth metal cation, and the like.

Throughout this specification, use of the terms "comprises" or "comprising" or grammatical variations thereon shall be taken to specify the presence of stated features, integers, steps or components but does not preclude the presence or addition of one or more other features, integers, steps, components or groups thereof not specifically mentioned.

Disclosed herein are advantageous compositions and process for the separation of DMBP isomers. The compositions and processes are based on zeolite adsorbents treated with metal cations in the +1 or +2 oxidation states.

Both natural and synthetic zeolites or zeolite analogues may be used as adsorbents in the processes of the present disclosure. An example of a zeolite encompassed by the present disclosure for use as an adsorbent comprises aluminosilicate cage structures in which the alumina and silica tetrahedra are intimately connected with each other in an open three-dimensional crystalline network. The tetrahedra are cross-linked by the sharing of oxygen atoms. The spaces between the tetrahedra are occupied by water molecules prior to dehydration. Subsequent partial or total dehydration results in crystals interlaced with channels of molecular dimensions. In the hydrated form, the crystalline aluminosilicates may be represented by the formula

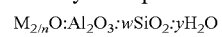

$M_{2/n}O:Al_2O_3:wSiO_2:yH_2O$ where M is a metal cation which balances the electrovalence of the tetrahedra, n represents the valence of the metal cation, w represents the mols of $SiO_2$ and Y, the mols of water. The metal cations may be any one of a number of cations such as for example the alkali metal cations or the alkaline earth cations or other selected metal cations.

Zeolites which find use as adsorbents in the process of the present disclosure may possess relatively well-defined pore structure. The exact zeolite type may be generally referred to by the particular silica-alumina ratio and the pore dimensions of the cage structures. For example, the faujasites are commonly represented as type X and type Y aluminosilicates and are defined by their varying silica to alumina ratios.

Specific structure types of zeolites which may be utilized in the process of the present disclosure include structure types BEA, FAU, MFI, MEL, MTW, MOR, LTL, EMT, FER, MAZ, MEI, TON, MWW, EUO, MFS, IMF, MRE, ITN, MTT, MSE and IWV.

Cationic exchange or base exchange methods are generally known to those familiar with the field of zeolite production and are generally performed by contacting a zeolite with an aqueous solution of soluble salts of the cation or cations desired to be exchanged on the zeolite. The desired degree of cation exchange is allowed to take place before the zeolite is removed from the aqueous solution and dried to a desired water content. It is contemplated that in cationic exchange or base exchange methods that the cation exchange may take place using individual solutions of desired cations to be placed on the zeolite or can use exchange solutions containing mixtures of the cations which are desired to be exchanged onto the zeolite. Multiple exchange steps may be necessary in order to achieve a desired cation loading.

Zeolite adsorbents for use in the processes of the present disclosure may comprise one or more metal cations in the +1 or +2 oxidation states.

Preferably the metal cations are selected from the group consisting of potassium, rubidium, cesium, barium, copper, silver, lithium, sodium, beryllium, magnesium, calcium, strontium, cadmium, cobalt, nickel, manganese and zinc and combinations thereof.

In one preferred embodiment of the separation process herein disclosed when the separation of 3,3'-DMBP from its isomeric mixtures is desired improved results can be attained by choosing a potassium and/or barium cation treated X or Y zeolite or mixtures thereof and performing the separation in iso-octane solvent. This system displays a pronounced selectivity for the adsorption of 3,3'-DMBP as compared to 3,4'-DMBP and 4,4'-DMBP.

In another preferred embodiment of the separation process herein disclosed when the separation of 3,4'-DMBP from its isomeric mixtures is desired improved results can be attained by choosing a cesium cation treated X or Y zeolite and performing the separation in mesitylene. This system displays a pronounced selectivity for the adsorption of both 3,3'-DMBP and 4,4'-DMBP compared to 3,4'-DMBP.

In another preferred embodiment of the separation process herein disclosed when the preferred adsorption of 4,4'-DMBP from its isomeric mixtures is desired improved results can be attained by choosing a potassium cation treated X, Y or Beta zeolite and performing the separation in iso-octane. This system displays a pronounced selectivity for the adsorption of 4,4'-DMBP as compared to 3,3'-DMBP and 3,4'-DMBP.

In separating the 3,3'-DMBP isomer in the process of this disclosure a bed of solid adsorbent may be contacted with a feed mixture, the 3,3'-DMBP is preferentially adsorbed on the adsorbent, the unadsorbed or raffinate mixture is removed from the adsorbent bed, and the adsorbed 3,3'-DMBP is removed from the solid adsorbent.

In separating the 4,4'-DMBP isomer in the process of this disclosure a bed of solid adsorbent may be contacted with a feed mixture, the 4,4'-DMBP is preferentially adsorbed on the adsorbent, the unadsorbed or raffinate mixture is removed from the adsorbent bed, and the adsorbed 4,4'-DMBP is removed from the solid adsorbent.

In separating the 3,4'-DMBP isomer in the process of this disclosure a bed of solid adsorbent may be contacted with a feed mixture, the 3,3'-DMBP and 4,4'-DMBP are preferentially adsorbed on the adsorbent, the unadsorbed 3,4-DMBP is removed from the adsorbent bed, and the adsorbed 3,3'-DMBP and 4,4'-DMBP removed from the solid adsorbent.

The solvent used in the adsorptive separations of the processes of the present disclosure is preferably a material that is separable from the mixture that is fed to the solid adsorbent. In desorbing the adsorbed component of the mixture, both the solvent and the desorbed component are removed from the adsorbent as a mixture, and without a method of separation of these two materials the purity of the adsorbed component of the feed would not be very high. Therefore, it is contemplated that a solvent that is of a different boiling range than the feed mixture fed to the solid adsorbent be used in this separation process. The use of a solvent of a differing boiling range would allow fractionation or other separation methods to be used to separate the selectively adsorbed feed component as a relatively pure product stream and allow recovery of the solvent for possible recycle in the process.

Solvents which can be used in the process of the present disclosure include, for example, iso-octane and mesitylene. Iso-octane and mesitylene have boiling points of 99 and 165° C. respectively, whereas 3,3'-DMBP, which is the lowest boiling DMBP isomer, boils at around 289° C.

The adsorbent can be contained in a single vessel where, through programmed flow into and out of the vessel, a separation of a desired DMBP isomer is effected. Swing bed operational techniques where a series of adsorbent vessels are available or simulated moving bed countercurrent operations may be used. In the latter method of operations the selection of a suitable solvent requires that it be capable of readily displacing a particular adsorbed DMBP isomer from the adsorbent.

The disclosure will now be more particularly described with reference to the following examples and FIGS. 1 to 8.

Preparation of Zeolite Adsorbents

The following general method was followed. About 100 g of NaY zeolite (Grace-Davison) was mixed with about 1000 g of a 0.4 M solution of the metal chloride in water. The mixture was stirred for 1 hr at ambient temperature, filtered and the filter cake washed with 3 L of water. The procedure was repeated using a 0.2 M metal chloride solution in water and the filter cake dried at 100° C. and then calcined in air for 2 hours at 300° C. The process was repeated twice more using 0.2 M metal chloride solution and the final filter cake dried at 110° C. Elemental compositions of some of the adsorbents prepared are shown in Table 3. USY 390 is a comparative example. The remaining zeolites are examples according to the present disclosure.

TABLE 3

Elemental composition of zeolites used in adsorption experiments

| Mole ratio | USY 390 | NaY | MgY | KY | SrY | CsY | KBeta |
|---|---|---|---|---|---|---|---|
| Si/Al | 315 | 2.42 | 2.55 | 2.44 | 2.55 | 2.56 | 5.16 |
| Na/Al | 0.23 | 0.98 | 0.19 | 0.07 | 0.11 | 0.26 | 0 |
| Mg/Al | 0 | 0 | 0.39 | 0 | 0 | 0 | 0 |
| K/Al | 0 | 0 | 0 | 0.94 | 0 | 0 | 0.93 |
| Sr/Al | 0 | 0 | 0 | 0 | 0.47 | 0 | 0 |
| Cs/Al | 0 | 0 | 0 | 0 | 0 | 0.65 | 0 |

Batch Adsorption Experiments

Various adsorbents were evaluated for the separation of dimethyl biphenyl (DMBP) isomer mixtures utilizing batch experiments. The adsorbents were dried under vacuum at 220° C. The dried solid materials were placed in a vial along with DMBP mixture solution. The DMBP mixture solution was prepared by diluting a mixture of the isomers comprising about 25% by weight 3,3'-isomer, 55% by weight 3,4'-isomer and 20% by weight 4,4'-isomer in a solvent such as isooctane or mesitylene. The total DMBP isomer content in the starting liquid phase was about 10% by weight. All the preparations were performed in an inert atmosphere dry box to minimize moisture exposure. The liquid/solid mixture was then agitated in a shaker at room temperature overnight (>16 hrs). The supernatant liquid phase was subsequently analyzed by gas chromatography (GC) to obtain the DMBP concentration. Solvents used were ACS grade or higher as available. DMBP isomer mixtures were either synthesized in house via methods described in, for example, WO 2015/112252, or prepared using purchased pure isomers.

Isolation of 3,4'-DMBP

FIG. 1 illustrates the results of batch adsorption experiments with various solvents and utilizing Y zeolite treated with potassium cations. The solvents examined were 1,3,5-trimethylbenzene (1,3,5-TMB), 1,2,4-trimethylbenzene (1,2,4-TMB), iso-octane, n-heptane, p-xylene, ethylbenzene and n-propylbenzene. For each solvent the amount of each DMBP isomer adsorbed is indicated in mmol/g. The larger the bar the more of a particular isomer is adsorbed. For each solvent the bars represent 3,3'-DMBP, 3,4'-DMBP and 4,4'-DMBP from left to right respectively. It is apparent that the solvent choice causes different adsorption selectivity for different DMBP isomers. In the cases of 1,2,4-TMB and p-xylene no adsorption of any of the isomers was observed. Use of mesitylene (1,3,5-trimethylbenzene) shows selective adsorption of 3,3'- and 4,4'-DMBP. This unique selectivity allows isolation of 3,4'-DMBP from the mixture. Use of paraffinic solvents, like isooctane and n-heptane, results in a greater adsorption of 3,3'-DMBP.

Isolation of 4,4'-DMBP

Figure 2:
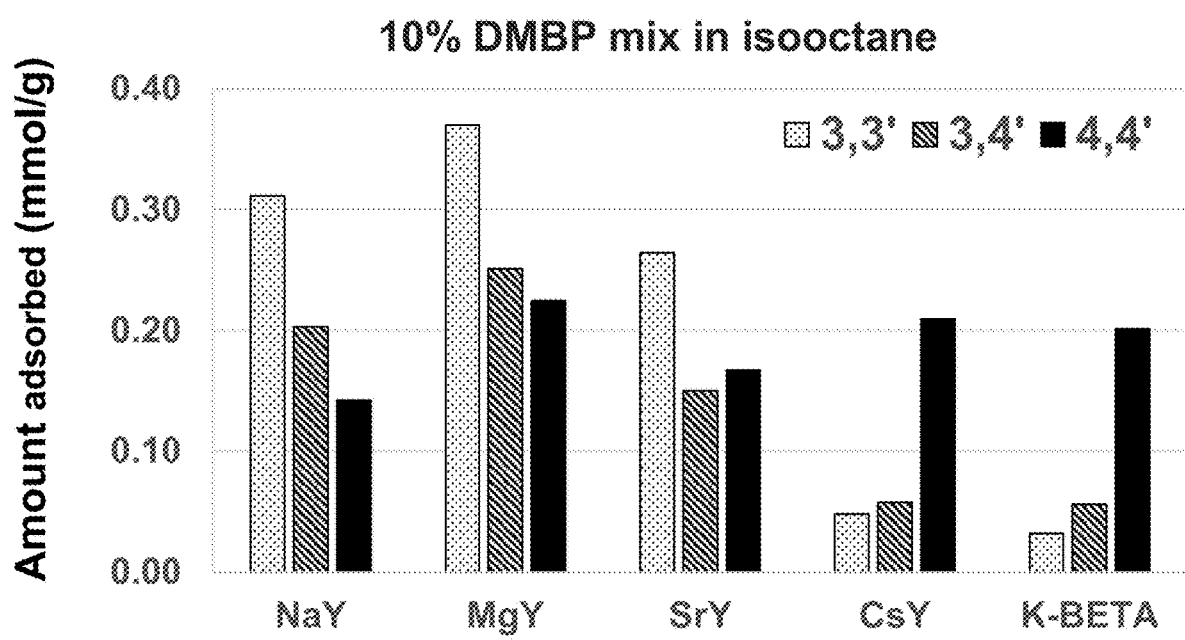
FIG. 2 is a bar chart illustrating the relative adsorptions of 3,3'-DMBP, 3,4'-DMBP and 4,4'-DMBP with various metal cation containing Y zeolites and K-Beta zeolite using isooctane as a solvent.

FIG. 2 illustrates the results of batch adsorption experiments with isooctane as a solvent and sodium, magnesium, strontium and cesium treated Y zeolite and potassium treated Beta zeolite. The cesium treated Y zeolite (CsY) adsorbs the 4,4'-isomer more selectively than the other two isomers. This is surprising because other cation treated Y zeolites such as sodium Y (NaY), magnesium Y (MgY) and strontium Y (SrY) adsorb the 3,3'-isomer more preferentially as found for KY. Adsorption of the 4,4'-isomer on CsY was three to four times higher than that of the other two isomers. Further, Beta zeolite treated with potassium cations indicated strong adsorption of the 4,4'-isomer.

Figure 3:
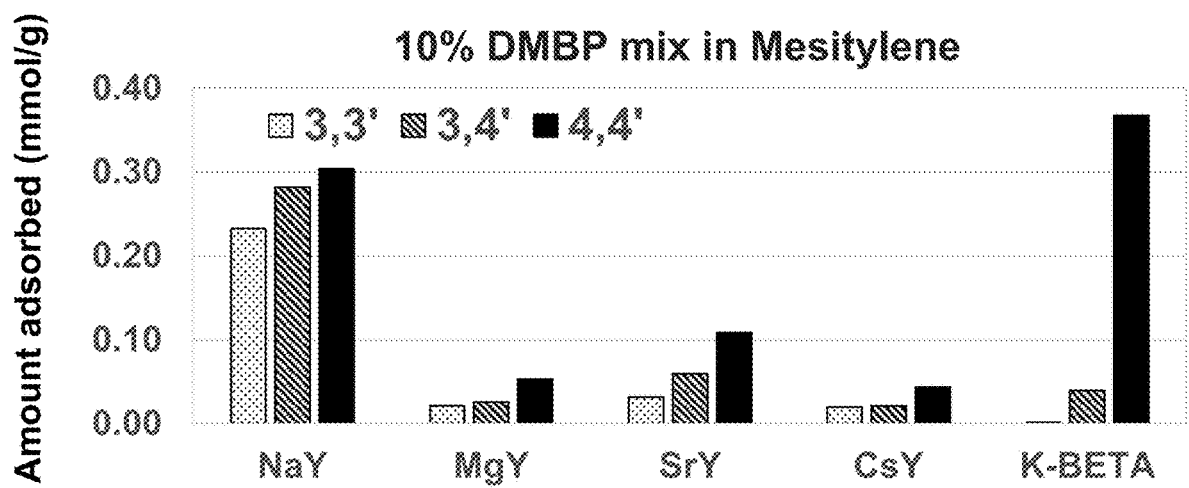
FIG. 3 is a bar chart illustrating the relative adsorptions of 3,3'-DMBP, 3,4'-DMBP and 4,4'-DMBP with various metal cation containing Y zeolites and K-Beta zeolite using mesitylene as a solvent.

FIG. 3 illustrates the results of batch adsorption experiments with mesitylene as a solvent and sodium, magnesium, strontium and cesium treated Y zeolite and potassium treated Beta zeolite. Use of mesitylene causes selective adsorption of the 4,4'-isomer on all of these zeolites. Adsorption of the 4,4'-isomer on the adsorbents was twice or more as compared to that of the other two isomers. Some of the adsorptions of DMBP with mesitylene solvent were lower than those obtained with isooctane solvent, however K-Beta zeolite showed high and very selective adsorption of the 4,4'-isomer.

Continuous Breakthrough Experiments

A liquid chromatographic system was used for the breakthrough study of the adsorbents at elevated temperature. Adsorbents were packed into 4.6 mm ID×100 mm long stainless steel columns with 0.5 micron frits at each end. The adsorbents were dried at 300° C. for 1 hour in a flow of dry nitrogen. A packed column was equilibrated at 150° C. or 177° C. with a solvent (i.e. the mobile phase) prior to injection. The DMBP mixture solution (10 wt. % or 25 wt. %) was prepared in the same solvent as the mobile phase and introduced to a column through injection of a 6.6 ml pulse. The flow rate of solvent was set at 0.4 ml/min. Effluent from the column was collected in a fraction collector and the concentrations of DMBP in the fractions were determined by GC.

Isolation of 3,3'-DMBP

Figure 4:
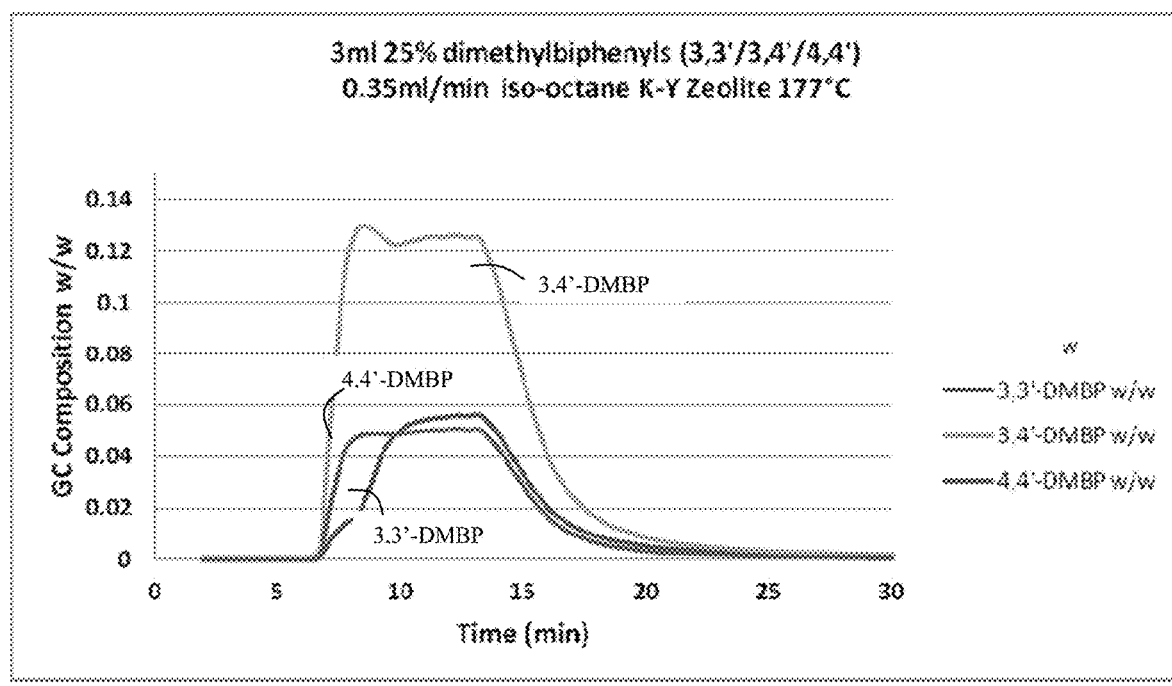
FIG. 4 illustrates the breakthrough curves for a mixture of 3,3'-DMBP, 3,4'-DMBP and 4,4'-DMBP in iso-octane solvent fed into a column containing Y zeolite containing potassium cations at 177° C.

A 3 ml pulse of 25 wt. % DMBP isomer mixture in iso-octane was introduced to a column containing potassium zeolite (Y-zeolite). FIG. 4 illustrates the breakthrough curves. The 3,3'-isomer was clearly retained as compared to the 4,4'-isomer and the 3,4'-isomer.

Figure 5:
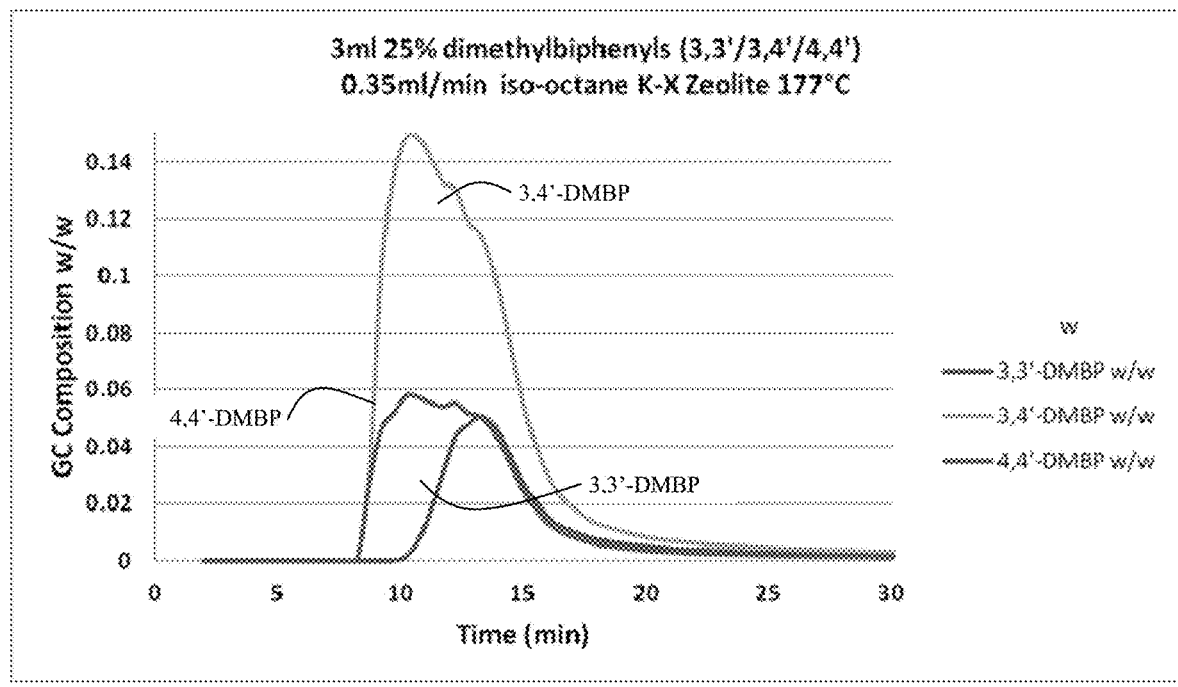
FIG. 5 illustrates the breakthrough curves for a mixture of 3,3'-DMBP, 3,4'-DMBP and 4,4'-DMBP in iso-octane solvent fed into a column containing X zeolite containing potassium cations at 177° C.

A 3 ml pulse of 25 wt. % DMBP isomer mixture in iso-octane was introduced to a column containing potassium zeolite (X-zeolite). FIG. 5 illustrates the breakthrough curves. The 3,3'-isomer was clearly retained as compared to the 4,4'-isomer and the 3,4'-isomer.

Figure 6:
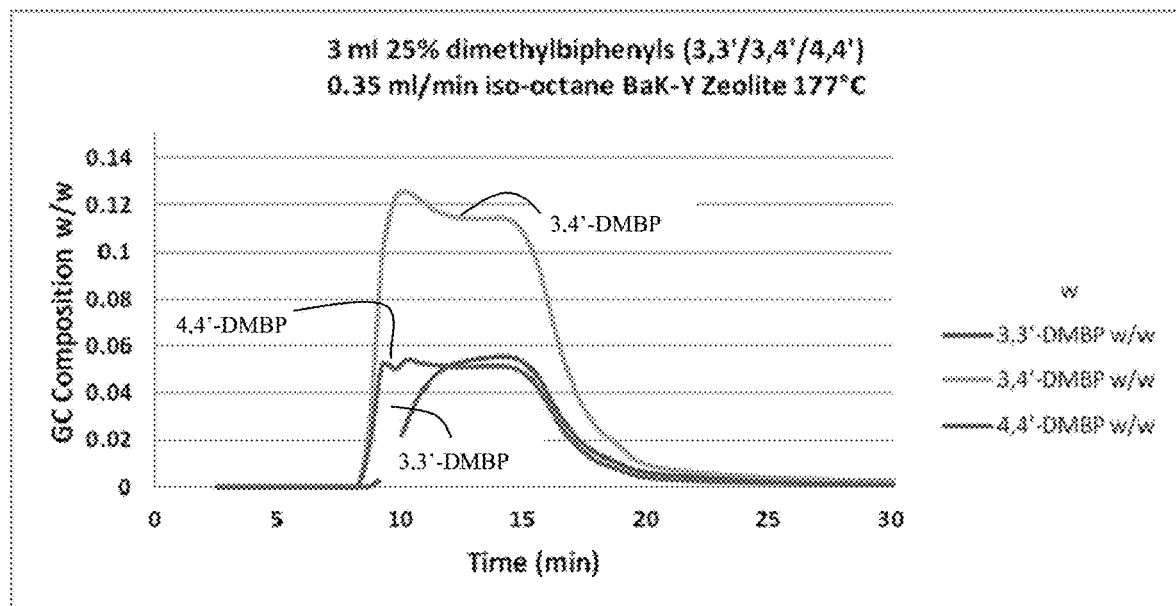
FIG. 6 illustrates the breakthrough curves for a mixture of 3,3'-DMBP, 3,4'-DMBP and 4,4'-DMBP in iso-octane solvent fed into a column containing Y zeolite containing potassium and barium cations at 177° C.

A 3 ml pulse of 25 wt. % DMBP isomer mixture in iso-octane was introduced to a column containing potassium barium zeolite (Y-zeolite). FIG. 6 illustrates the breakthrough curves. The 3,3'-isomer was clearly retained as compared to the 4,4'-isomer and the 3,4'-isomer.

Figure 7:
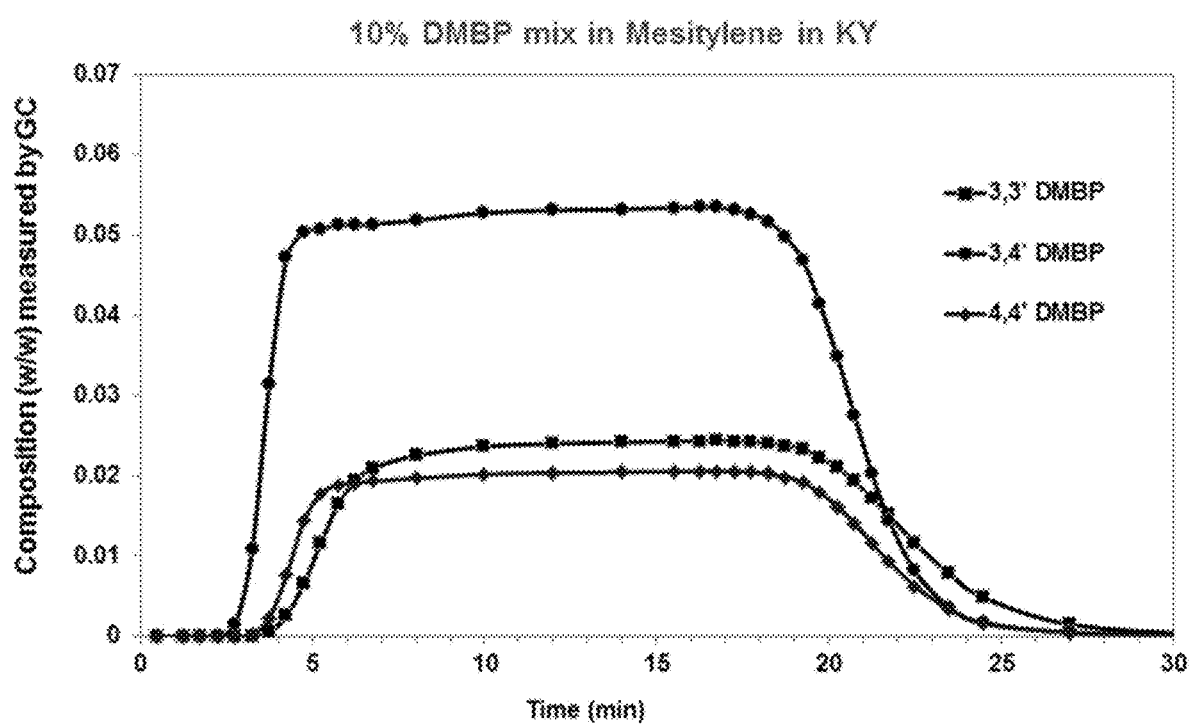
FIG. 7 illustrates the breakthrough curves for a mixture of 3,3'-DMBP, 3,4'-DMBP and 4,4'-DMBP in mesitylene solvent fed into a column containing Y zeolite containing potassium cations at 150° C.

Separation of the DMBP mixture on the KY zeolite with mesitylene was further tested in a liquid chromatographic system to validate the batch experiment data at elevated temperature (150° C.). As shown in FIG. 7, the breakthrough point of the 3,4' isomer is earlier than the other two isomers. This indicates no adsorption of the 3,4' isomer, while the other two isomers show delayed breakthrough points due to their retention. The selective adsorption of the two isomers is consistent with what was observed from the batch experiment. The non-adsorbed isomer may be removed from the adsorbent and the adsorbed two isomers then recovered by desorption. The data also shows the 3,3'-isomer is preferred to the 4,4'-isomer, thus presenting the possibility of separation of these two isomers into individual components.

Comparative Example

Figure 8:
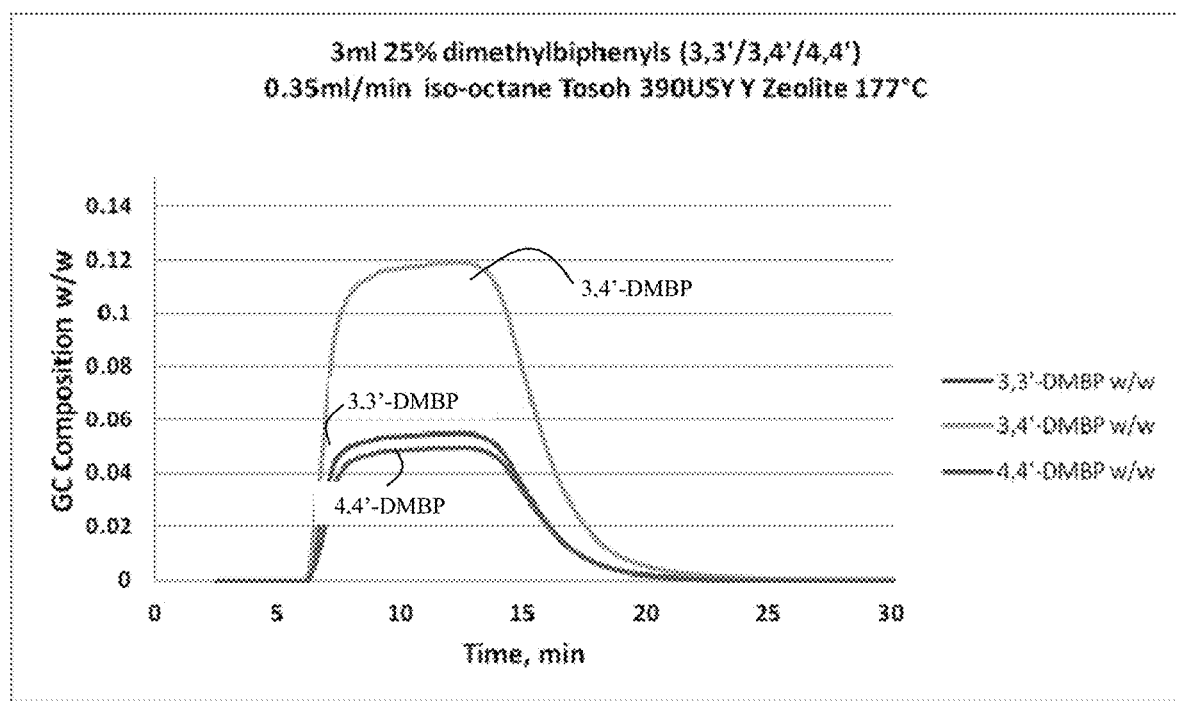
FIG. 8 illustrates the breakthrough curves for a mixture of 3,3'-DMBP, 3,4'-DMBP and 4,4'-DMBP in iso-octane solvent fed into a column containing high silica USY at 177° C.

For comparison, and to illustrate the effect of the metal cations in the zeolite, a high silica low metal cation faujasite (390 USY) was packed into a column and tested. This material has a high Si/Al ratio of 315 and a low Na/Al ratio of 0.23. FIG. 8 illustrates no selectivity for any of the DMBP isomers over the others.

It is to be understood that while the present disclosure has been described in conjunction with the specific embodiments thereof, the foregoing description is intended to illustrate and not limit the scope of the disclosure. Other aspects, advantages and modifications will be apparent to those skilled in the art to which the disclosure pertains. Therefore, the above examples are put forth to provide those skilled in the art with a complete disclosure and description of how to use the disclosed processes, and are not intended to limit the scope of the disclosure.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

All documents cited herein are fully incorporated by reference for all jurisdictions in which such incorporation is permitted and to the extent such disclosure is consistent with the description of the present disclosure.

The invention claimed is:

1. A process for separating one or more of the dimethyl biphenyl (DMBP) isomers, 3,3'-DMBP, 3,4'-DMBP and/or 4,4'-DMBP from a mixture comprising two or more of said isomers, the process comprising a step of contacting said mixture with an adsorbent comprising at least one zeolite, wherein said zeolite comprises one or more metal cations in the +1 or +2 oxidation states, and said process results in the separation of at least one of 3,3'-DMBP, 3,4'-DMBP, and 4,4'-DMBP from said mixture.

2. A process according to claim 1, wherein the zeolite has a largest diffuse along dimension of at least about 4.0 Å.

3. A process according to claim 1, wherein the largest diffuse along dimension of the zeolite is at least about 4.5 Å, or at least about 5.0 Å, or at least about 5.5 Å, or at least about 6.0 Å, or at least about 6.5 Å, or at least about 7.0 Å.

4. A process according to claim 1, wherein the largest diffuse along dimension of the zeolite is between about 4.0 Å and about 8.0 Å, or between about 4.5 Å and about 8.0 Å, or between about 5.0 Å and about 8.0 Å, or between about 5.5 Å and about 8.0 Å, or between about 6.0 Å and about 8.0 Å, or between about 6.5 Å and about 8.0 Å.

5. A process according to claim 1, wherein the zeolite structure type comprises BEA, FAU, MFI, MEL, MTW, MOR, LTL, EMT, FER, MAZ, MEI, TON, MWW, EUO, MFS, IMF, MRE, ITN, MTT, MSE or IWV.

6. A process according to claim 1, wherein the zeolite comprises a 12-ring zeolite, an 11-ring zeolite or a 10-ring zeolite.

7. A process according to claim 1, wherein the zeolite comprises an X type zeolite, a Y type zeolite or a Beta type zeolite.

8. A process according to claim 1, wherein the Si/Al ratio of the zeolite is less than about 200, or less than about 100, or less than about 50, or less than about 20, or less than about 10.

9. A process according to claim 1, wherein the zeolite comprises one or more alkali metal cations, alkaline earth metal cations, transition metal cations, rare earth metal cations or combinations thereof.

10. A process according to claim 1, wherein the ionic radius of the metal cation is between about 0.8 Å and about 2.0 Å.

11. A process according to claim 1, wherein the zeolite comprises one or more of $Na^+$, $K^+$, $Rb^+$, $Cs^+$, $Mg^{2+}$, $Ca^{2+}$, $Sr^{2+}$ and $Ba^{2+}$ cations.

12. A process according to claim 1, wherein the molar ratio of all metal cations in the +1 and/or +2 oxidation states relative to aluminum in the zeolite is between about 0.01 and about 2.0, or between about 0.05 and about 1.5, or between about 0.1 and about 1.5, or between about 0.25 and about 1.5.

13. A process according to claim 1, wherein the molar ratio of all metal cations in the +1 and/or +2 oxidation states relative to aluminum in the zeolite is greater than about 0.27, or greater than about 0.30, or greater than about 0.40, or greater than about 0.45, or greater than about 0.50.

14. A process according to claim 1, wherein the sodium/aluminum molar ratio of the zeolite is less than about 1.0, or less than about 0.8, or less than about 0.6, or less than about 0.4, or less than about 0.3, and wherein the zeolite contains at least one other metal cation.

15. A process according to claim 1, wherein the molar ratio of metal cations in the +1 and/or +2 oxidation states relative to aluminum in the zeolite, said metal cations being other than sodium(+), is greater than about 0.1, or greater than about 0.2, or greater than about 0.3, or greater than about 0.4.

16. A process according to claim 1, wherein the average crystalline size of the zeolite is less than about 5000 nm, or less than about 2000 nm, or less than about 1000 nm, or less than about 500 nm, or less than about 200 nm, or less than about 100 nm, or less than about 50 nm.

17. A process according to claim 1, wherein the average crystalline size of the zeolite is from about 1 to about 5000 nm, or from about 1 to about 2000 nm, or from about 1 to about 1000 nm, or from about 5 to about 500 nm, or from about 10 to about 100 nm.

18. A process according to claim 1, wherein the mixture of DMBP isomers further comprises one or more solvents.

19. A process according to claim 18, wherein the solvent is a saturated hydrocarbon, an aromatic hydrocarbon or mixtures thereof.

20. A process according to claim 18, wherein the solvent comprises an aliphatic hydrocarbon solvent having a kinetic diameter greater than about 4.5 Å, or greater than about 5.0 Å, or greater than about 5.5 Å, or greater than about 6.0 Å.

21. A process according to claim 18, wherein the solvent comprises an aromatic hydrocarbon solvent having a kinetic diameter greater than about 6.0 Å, or greater than about 6.5 Å, or greater than about 7.0 Å, or greater than about 7.5 Å.

22. A process according to claim 1, wherein the process comprises separating 3,3'-DMBP from a mixture comprising 3,3'-DMBP, 3,4'-DMBP and 4,4'-DMBP.

23. A process according to claim 1, wherein the process comprises separating 3,4'-DMBP from a mixture comprising 3,3'-DMBP, 3,4'-DMBP and 4,4'-DMBP.

24. A process according to claim 1, wherein the process comprises separating 4,4'-DMBP from a mixture comprising 3,3'-DMBP, 3,4'-DMBP and 4,4'-DMBP.

25. A process according to claim 1, wherein the process comprises separating 3,3'-DMBP from a mixture comprising 3,3'-DMBP, 3,4'-DMBP and 4,4'-DMBP and wherein the zeolite comprises barium cations.

26. A process according to claim 1, wherein the process comprises separating 3,3'-DMBP from a mixture comprising 3,3'-DMBP, 3,4'-DMBP and 4,4'-DMBP, wherein the zeolite comprises barium cations and wherein the solvent comprises iso-octane.

27. A process according to claim 1, wherein the process comprises separating 3,4'-DMBP from a mixture comprising 3,3'-DMBP, 3,4'-DMBP and 4,4'-DMBP, wherein the zeolite comprises potassium cations.

28. A process according to claim 1, wherein the process comprises separating 3,4'-DMBP from a mixture comprising 3,3'-DMBP, 3,4'-DMBP and 4,4'-DMBP, wherein the zeolite comprises potassium cations and wherein the solvent comprises 1,3,5-trimethylbenzene.

29. A process according to claim 1, wherein the process comprises separating 4,4'-DMBP from a mixture comprising 3,3'-DMBP, 3,4'-DMBP and 4,4'-DMBP and wherein the zeolite comprises cesium cations.

30. A process according to claim 18, wherein the process comprises separating 4,4'-DMBP from a mixture comprising 3,3'-DMBP, 3,4'-DMBP and 4,4'-DMBP, wherein the zeolite comprises cesium cations and wherein the solvent comprises iso-octane.

31. A process according to claim 1, wherein the process is performed between about 20° C. and about 250° C., preferably above about 115° C.

32. A process according to claim 1, wherein the process is performed in batch or continuous mode.

33. A process according to claim 1, wherein the contact time between the zeolite and the DMBP mixture is between a few seconds and several hours, or between a few minutes and several hours, or between about 0.5 hours and about 10 hours, or between about 0.5 hours and about 5 hours.

34. A process according to claim 18, wherein the difference between the boiling point of the solvent or solvents and the boiling point of any one of the 3,3'-DMBP, 3,4'-DMBP and 4,4'-DMBP isomers is greater than about 100° C., or greater than about 75° C., or greater than about 50° C., or greater than about 25° C.

* * * * *